United States Patent [19]

Culler

[11] Patent Number: 5,393,362
[45] Date of Patent: * Feb. 28, 1995

[54] METHOD FOR IMPROVING ADHESION TO METAL

[75] Inventor: Scott R. Culler, Burnsville, Minn.

[73] Assignee: Minnesota Mining and Manufacturing Company, St. Paul, Minn.

[*] Notice: The portion of the term of this patent subsequent to Apr. 30, 2008 has been disclaimed.

[21] Appl. No.: 985,633

[22] Filed: Dec. 3, 1992

Related U.S. Application Data

[63] Continuation of Ser. No. 653,616, Feb. 11, 1991, Pat. No. 5,190,795, which is a continuation-in-part of Ser. No. 407,365, Sep. 14, 1989, Pat. No. 5,011,410.

[51] Int. Cl.⁶ .................... B05D 3/12; B05D 5/10; C23C 18/02
[52] U.S. Cl. ................................ 156/153; 148/284; 156/314; 427/226; 427/290; 427/318
[58] Field of Search .............. 437/208, 212; 427/226, 427/290, 289, 318, 327, 330, 343, 344; 156/325, 153, 314; 148/284

[56] References Cited

U.S. PATENT DOCUMENTS

| | | |
|---|---|---|
| 2,991,204 | 7/1961 | Astle .................... 148/248 |
| 3,214,302 | 10/1965 | Brodt et al. . |
| 4,028,325 | 6/1977 | King et al. . |
| 4,230,773 | 10/1980 | Bakos . |
| 4,364,731 | 12/1982 | Norling et al. . |
| 4,365,359 | 12/1982 | Raab . |
| 4,499,152 | 2/1985 | Green et al. . |
| 4,503,093 | 3/1985 | Iseli et al. . |
| 4,600,390 | 7/1986 | Gobel et al. . |
| 4,648,845 | 3/1987 | Orlowski et al. . |
| 4,673,354 | 6/1987 | Culler . |
| 4,681,538 | 7/1987 | DeLuca et al. . |
| 4,684,555 | 8/1987 | Neumeyer . |
| 4,808,483 | 2/1989 | Nakasuji et al. . |
| 4,826,430 | 5/1989 | Chen et al. . |
| 4,895,516 | 1/1990 | Hulten . |
| 4,933,202 | 6/1990 | Rheinberger et al. . |
| 4,935,265 | 6/1990 | Pike . |
| 4,940,607 | 7/1990 | Culler et al. . |
| 4,983,422 | 1/1991 | Davis et al. . |
| 5,011,410 | 4/1991 | Culler et al. . |
| 5,190,795 | 3/1993 | Culler ........................... 427/226 |

FOREIGN PATENT DOCUMENTS

| | | |
|---|---|---|
| 264353A | 9/1988 | European Pat. Off. . |
| 3642290C1 | 12/1986 | Germany . |
| 3802042 | 7/1989 | Germany . |
| 3802043 | 7/1989 | Germany . |
| 88/03405 | 5/1988 | WIPO . |

OTHER PUBLICATIONS

Patent Abstracts of Japan, vol. 13, No. 431 (C-640)(3779), 26 Sep. 1989, based on JP-A-1,165,775 published 29 Jun. 1989 (Iwama).

*Primary Examiner*—Caleb Weston
*Attorney, Agent, or Firm*—Gary L. Griswold; Walter N. Kirn; Douglas E. Reedich

[57] ABSTRACT

A method of applying a layer of exogenous inorganic oxide to a metal article which method involves heating a coating of a coupling agent for a temperature and for a time sufficient to convert the coating to a layer of exogenous inorganic oxide. Also a method of adhering a metal article to an adhesive and/or a composite and a method of adhering a metal article to a substrate.

14 Claims, No Drawings

METHOD FOR IMPROVING ADHESION TO METAL

This is a continuation of application Ser. No. 07/653,616, filed Feb. 11, 1991, now U.S. Pat. No. 5,190,795, which is a continuation-in-part of commonly assigned application 07/407,365, filed on Sep. 14, 1989, U.S. Pat. No. 5,011,410, incorporated herein by reference.

BACKGROUND OF THE INVENTION

1. Field of the Invention

This invention relates to articles with a layer of exogenous inorganic oxide thereon. In another aspect, this invention relates to methods of applying a layer of exogenous inorganic oxide to the surface of an article. In yet another aspect, this invention relates to methods for adhering a metal article to a substrate by way of an intermediate adhesive.

2. Description of the Related Art

Methods of enhancing the bonding of polymeric substances to substrates via silane coupling agents are disclosed in U.S. Pat. No. 4,364,731 (Norling et al.). These methods involve depositing an oxide layer such as alumina or silica onto a substrate, applying a layer of silane coupling agent to the oxide layer, then coating or contacting the layer of silane coupling agent with a polymeric substance. Stainless steel is among the disclosed substrate materials, the preferred oxide coating is silica, and the preferred method for applying the silica coating is sputter deposition.

U.S. Pat. No. 4,681,538 (DeLuca et al.) discloses a method for applying a crystalline alumina orthodontic bracket to the teeth of a patient. The method involves coating the tooth-contacting surface of the bracket with a thin adherent coating of a siliceous material. Methods disclosed for applying the coating of siliceous material include cathode sputtering, plasma deposition, and electron beam deposition. A bracket so coated can be further coated with a silane coupling agent and adhered via an acrylic orthodontic cement to the tooth of a patient.

U.S. Pat. No. 4,230,773 (Bakos) discloses a method for reducing the porosity and surface roughness of a ceramic substrate. The method involves coating the surface of the substrate with organosilicon compounds, drying the coated substrate, and then subjecting the coated substrate to elevated temperature so as to convert the organosilicon compounds to silicon oxides.

SUMMARY OF THE INVENTION

This invention provides a method for applying a layer of exogenous inorganic oxide to the surface of a metal article, which method comprises the steps of:

(a) coating at least a portion of the surface of the article with a coupling agent that is capable on heating of converting to exogenous inorganic oxide; and (b) heating the coated surface at a temperature and for a time sufficient to convert the coating to a layer of exogenous inorganic oxide.

This invention further provides a method for adhering a metal article to an adhesive and/or a composite, which method comprises steps (a) and (b) set forth above and the further step of:

(c) adhering the metal article at said layer of exogenous inorganic oxide to an adhesive and/or a composite.

This invention also provides a method for adhering a metal article to a substrate by way of an intermediate layer of adhesive, which method comprises the steps of:

(a) coating at least a portion of the surface of the metal article with a coupling agent that is capable on heating of converting to exogenous inorganic oxide;

(b) heating the coated surface at a temperature and for a time sufficient to convert the coating to a layer of exogenous inorganic oxide;

(c) adhering the metal article at said layer of exogenous inorganic oxide to an intermediate layer of adhesive; and (d) adhering the substrate to the article by way of the intermediate layer.

Preferred embodiments of the invention also involve the preliminary step of toughening the surface of the article prior to the application of the coupling agent.

A layer of exogenous inorganic oxide applied to a metal article according to the method set forth above affords an article that exhibits strong adhesion to conventional adhesives and dental composites.

DETAILED DESCRIPTION OF THE INVENTION

As used herein, the term "silica" designates material consisting essentially of silicon oxides, and the terms "silane" and "organosilicon compound" are synonymous. Further, as used herein the phrase "exogenous inorganic oxide" designates an oxide that is chemically unrelated to the metal or metals of the article, and is not produced by oxidizing the surface of the article with oxygen.

Articles comprising conventional metals and metal alloys are suitable for use in this invention. For example, any type of stainless steel, e.g., martensitic, ferritic, or austenitic stainless steel, is suitable, as are other conventional metals such as gold, palladium, platinum, chromium, nickel, and silver, mixtures thereof, and alloys containing such metals.

Any article comprising a surface of such a metal can be used in this invention. Articles that are intended to be adhered to an adhesive and/or a composite can be used. For example, a glass-lined stainless steel reactor, having a crack in the glass lining such that the underlying stainless steel surface is exposed, can be repaired using the methods of the invention. The stainless steel surface can be prepared using the method for applying a layer of exogenous inorganic oxide (described in detail below). A curable composite can then be applied to the prepared surface and cured to afford a repaired reactor having no exposed stainless steel surface.

Articles that are intended to be adhered to a substrate by way of an intermediate adhesive can also be used in this invention. For example a metal article can be adhered to a curable composite generally as described above but using an intermediate adhesive layer between the prepared surface and the composite. Other articles that can be used include those that can be adhered to dental substrates such as dentin or enamel in dental (e.g., orthodontic, prosthetic, endodontic, and aesthetic) applications. Suitable dental articles include orthodontic articles such as brackets and arch wires, endodontic articles such as posts and retention pins, and fixed prostheses such as dental crowns, bridges, and the like, and splints for avulsed or mobile teeth.

The portion of the surface of a metal article that underlies the layer of exogenous inorganic oxide is preferably roughened. Sandblasting is the preferred method of roughening. Sandblasting the surface of the article is carried out in order to roughen the surface thereby producing more surface area for subsequent adhesion of the layer of exogenous inorganic oxide. Further, sandblasting allows the subsequently-applied coupling agent to wet the surface of the article better. Sandblasting, e.g., with 220 grit aluminum oxide with a PONY TM sandblaster for at least about 30 seconds is a preferred sandblasting procedure. Whether sandblasted or not, a metal article can optionally be etched with strong etchant (e.g., nitric, sulfuric, hydrofluoric, or hydrochloric acid) and washed with purified water and/or an organic solvent such as acetone in order to assure a clean surface.

In the case of an article comprising an oxidizable metal a further optional, preferred treatment involves heating the surface of the clean, preferably sandblasted article in an oxidizing atmosphere at a temperature and for a time sufficient to form an oxide layer on the surface of the article. The particular temperature and time preferred for this step is dependent on the nature of the metal, but generally a temperature of about 200° C. to about 1200° C., preferably at about 350° C. to about 1100° C. for a period of about 1 minute to about 60 minutes is suitable. Such heating can be carried out in a conventional furnace in the presence of air.

The layer of exogenous inorganic oxide can be applied by coating the article with a coupling agent or a mixture of coupling agents and pyrolyzing to convert the coupling agent to a layer of exogenous inorganic oxide. The particular structure of the coupling agent is not unduly critical to the method of the invention, as the organic functionality is ultimately removed in the pyrolysis step described in detail below. Suitable coupling agents include conventional titanate coupling agents, zirconate coupling agents, and silane coupling agents that are capable of affording titanium, zirconium, or silicon oxides upon pyrolysis. Organosilicon compounds (i.e., silane coupling agents) are preferred. Suitable organosilicon compounds include "A-151" vinyltriethoxysilane, "A-172" vinyltri-(2-methoxyethoxy)silane, "A-174" gamma-methacryloxypropyltrimethoxysilane, "A-186" 3,4-epoxycyclohexylmethyltrimethoxysilane, "A-187" gamma-glycidoxypropyltrimethoxysilane, and "A-189" gamma-mercaptopropyltrimethoxysilane (all commercially available from Union Carbide Corp.); "Z-6030" gamma-methacryloxypropyltrimethoxysilane, "Z-6040" gamma-glycidoxypropyltrimethoxysilane, "XZ-8-0951" gamma-mercaptopropyltrimethoxysilane (all commercially available from Dow Corning Corp.); "A0564" allyltriethoxysilane, "D4050" diallyldichlorosilane, "D6205" divinyldiethoxy-silane, "G6720" glycidoxypropyltriethoxysilane, "M8542" methacryloxypropyldimethylchlorosilane, and "S1588" m,p-styrylethyltrimethoxysilane (all commercially available from Petrarch Systems, Inc.); gamma-aminopropyltrimethoxy-silane, allyltrimethoxysilane, dimethyldiethoxysilane, dihydroxydiphenylsilane, triethoxysilane, trimethoxysilane, triethoxysilanol, 3-(2-aminoethylamino)propyl-trimethoxysilane, methyltrimethoxysilane, vinyltriacetoxy-silane, methyltriethoxysilane, tetraethyl orthosilicate, tetramethyl orthosilicate, ethyltriethoxysilane, amyltriethoxysilane, ethyltrichlorosilane, amyltrichloro-silane, phenyltrichlorosilane, phenyltriethoxysilane, methyltrichlorosilane, methyldichlorosilane, dimethyldi-chlorosilane, dimethyldiethoxysilane, and similar compounds, and mixtures thereof. If the organosilicon compound contains hydrolyzable functional groups such as alkoxy, acyloxy, or halogen, these functional groups can be hydrolyzed to form silanol groups if desired prior to the application of the compound to the surface of the article.

The coupling agent can be applied neat, but it is preferably applied from a solution thereof in a volatile organic solvent. Such a solution preferably contains from about 1% by weight to about 80%, more preferably from about 1% to about 10%, by weight of a coupling agent based on the total weight of the solution, the remainder consisting essentially of a solvent or a mixture of solvents. Examples of generally suitable solvents include alcohols such as methanol, ethanol, and propanol, ketones such as acetone and methyl ethyl ketone, hydrocarbons such as hexane, cyclohexane, toluene, and the like, ethers such as diethyl ether and tetrohydrofuran, and mixtures thereof. In addition, water can be present if desired, e.g., to hydrolyze a compound with hydrolyzable functional groups. An organic acid such as acetic acid can also be present if desired, e.g., to stabilize a solution containing a silanol.

Conventional silanol priming solutions such as those disclosed in U.S. Pat. No. 4,673,354 (Culler), the disclosure of which is incorporated hereby by reference, are suitable. A preferred commercially available solution for use in coating an article is SCOTCHPRIME TM ceramic primer (3M).

The coupling agent can be applied in any suitable manner, such as spraying, dip coating, or brush coating. If too little coupling agent is applied, the surface of the article might not be sufficiently coated, and optimal adhesion might not be achieved. On the other hand, if the coating of coupling agent is too thick the oxide resulting from the pyrolysis step will comprise oxide in the form of a powder. Again, optimal adhesion might not be achieved. The preferred amount of compound to be applied is therefore at least the amount that will coat substantially all of the surface intended to be adhered to the dental substrate, and less than the amount that will cause the formation of oxide in the form of a powder upon pyrolysis. More particularly, when the compound is applied from a solution, preferably about 2 to about 12 $\mu$L of a solution containing from about 1% by weight of coupling agent based on the total weight of the solution is applied per $cm^2$ of surface. Alternatively, lesser amounts of a more concentrated solution of coupling agent (e.g., in the range up to about 10% by weight) can be used. Once the coupling agent is applied, the solvent is removed by conventional means, e.g., air drying or mild heating in a drying oven (e.g., heating at 50° C. –100° C.).

The suitable range of temperature and time for the pyrolysis step depends only to a slight degree on the nature of the coupling agent. In general a temperature of between about 200° C. and 1200° C. for a period of about 1 minute to several hours (e.g., about 4 to about 5 hours) is suitable, the time and temperature required being inversely related to one another. Higher temperatures can be used with the caveat that the article must of course be stable to the temperature used. Also, excessively high temperatures tend to cause discoloration of the coated article. The preferred range of temperature is from about 200° C. to about 1200° C. The pyrolysis step can be carried out in a conventional oven such as a muffle oven or porcelain oven, either in the presence of air or in another oxidizing atmosphere. It is preferred that the resulting oxide layer be of sufficient thickness to provide improved adhesion of the article to a dental adhesive or composite relative to the adhesion of a like article absent the oxide layer.

A metal article prepared as described above can be adhered to an adhesive and/or a composite. An article can also be adhered to a substrate using an adhesive as an intermediate layer. It is preferred to apply a coupling agent such as a titanate, zirconate, or silane coupling agent to the layer of exogenous inorganic oxide on the surface of the article, and then apply a conventional adhesive and/or composite. Silane coupling agents are preferred. Silane coupling agents and methods for their use are well known to those skilled in the art and are disclosed for example in U.S. Pat. No. 4,673,354.

Representative adhesives include acrylate, methacrylate, urethane, and epoxy resins, such as those disclosed in U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,306,190, 4,327,014, 4,379,695, 4,387,240, and 4,404,150, the disclosures of which are incorporated herein by reference. Mixtures and derivatives of such resins are also useful. Preferred resins include mixtures of diglycidylmethacrylate of Bisphenol A ("Bis-GMA") and triethyleneglycol dimethacrylate ("TEGDMA").

Composites that can be used include conventional composites containing an adhesive resin as described above and a filler such as silica, glass, and the like. Commercially available composites include dental restorative composites such as P-50 TM and P-30 TM dental restoratives (3M).

Using the methods of this invention, a metal article adheres strongly to such adhesives and composites. Therefore, this invention reduces problems caused by failure of the adhesive bond between a metal article and an adhesive or a composite. Particular problems of this sort that can be addressed by this invention include loosening and dislodging of patch material adhered to the stainless steel substrate of a repaired glass-lined reactor. Also, the loss of permanent fixtures anchored by endodontic posts due to failure at the cement/post interface, and root fracture due to the presence of a non-bonded endodontic post can be addressed. Furthermore, the increased adhesion provided by this invention avoids the need to apply a wire mesh, undercut, or machine-textured surface to the metal article in order to achieve adequate adhesion.

The following examples are provided to illustrate the invention.

EXAMPLE 1

Samples of type 303 and type 17-4 stainless steel in the form of circular disks 2.54 cm in diameter were treated using the following steps:
1. Wet polishing one surface using a lapidary wheel first with 320 grit silicon carbide for 10 seconds and then with 600 grit silicon carbide for about 60 seconds;
2. Sandblasting the polished surface for 30 seconds using 220 grit aluminum oxide;
3. Rinsing the sandblasted surface with acetone and acid etching with SCOTCHGEL TM enamel etchant (a phosphoric acid based etchant, 3M) for 60 seconds, rinsing with deionized water and blow drying with compressed air;
4. Coating the surface with 30 μL of a 1% by weight hydrolyzed A-174 TM silane solution (prepared using the procedure of EXAMPLE 3 of U.S. Pat. No. 4,673,354) and allowing to dry at room temperature; and
5. Heating in a THERMOLYNE TM 10500 muffle oven (Sybron Corporation) at 350° C. for about 5 minutes.

The above treated samples were prepared for adhesion testing by bonding dimethacrylate-based composites to the prepared surfaces using the following procedure:
A. Coating the prepared surface with 20 μL of the silane solution of Step 4 above and drying in air at room temperature;
B. Brushing on about 10 mg of SILUX TM enamel bond adhesive (a methacrylate based dental adhesive, 3M) over the entire prepared surface and curing with a VISILUX TM 2 curing light (3M) for 20 seconds;
C. Applying approximately a 0.3 cm high cylindrical button of TRANSBOND TM adhesive (a methacrylate based dental adhesive, 3M Unitek) using a TEFLON TM polytetrafluoroethylene mold having a cross sectional area of 0.125 cm$^2$. The applied adhesive was cured using a VISILUX 2 curing light for 30 seconds; and
D. Allowing the metal disk and mold to stand at room temperature for about 5 minutes, then storing them in distilled water at 37° C. for 24 hours.

The mold was then carefully removed from the button, leaving the molded button attached to the metal disk. Adhesive strength was evaluated by mounting the metal disk in a holder clamped in the jaws of an INSTRON TM tensile testing apparatus with the bondline oriented parallel to the direction of pull. A loop of 0.44 mm diameter orthodontic wire was placed around the button adjacent to the treated metal surface. The ends of the orthodontic wire were clamped in the pulling jaw of the INSTRON apparatus, thereby placing the bond in shear stress. The bond was stressed until failure, using a crosshead speed of 2 mm/minute. The adhesion values were calculated using the following formula:

$$\text{Adhesion in Kg/cm}^2 = \frac{\text{Shear Force (in Kg)}}{\text{Area of the Mold (in cm}^2\text{)}}$$

The data in TABLE I show the effect of omitting steps from the above treatment procedure. The shear adhesion values for six samples were averaged to provide the value presented in TABLE I, except for Run 4, where the shear adhesion values of twelve samples were averaged.

TABLE I

| | Adhesion to Stainless Steel 303 and 17-4 | | |
|---|---|---|---|
| | | Shear Adhesion (Kg/cm$^2$) | |
| Run No. | Surface Preparation | 303 | 17-4 |
| 1 | Non-sandblasted, Steps 2, 4 & 5 omitted | 152 | 171 |
| 2 | Non-sandblasted, Step 2 omitted | 178 | 210 |
| 3 | Sandblasted, Step 4 omitted | 185 | 184 |
| 4 | Sandblasted, Steps 4 & 5 omitted | 216 | 220 |
| 5 | Sandblasted, no Steps omitted | 357 | 327 |

The data show that pyrolysing the organosilicon compound to afford a layer of silica increases the shear adhesion on both sandblasted and non-sandblasted samples. The increase, however, is more pronounced in a procedure involving sandblasting.

EXAMPLE 2

Various porcelain-fusing metal surfaces were prepared using the general procedure of EXAMPLE 1 with the following exceptions: in Step 1, the metal was dry polished; in Step 2, the surface was sandblasted for 1 minute; in Step 3, the samples were rinsed with distilled water only; an additional step (Step 3a) was added between Step 3 and Step 4, which consisted of heating the samples in a Ney STAR FIRE TM high performance programmable porcelain furnace (#949-14-002, J. M. Ney Company, Bloomfield, Conn.) at a particular furnace temperature for the respective metal substrate as follows: REXILLIUM TM III (Jeneric Industries, Inc., Wallingford, Conn.) and stainless steel 316 (3M Unitek) were heated at 1051° C., RX NATURELLE TM (Jeneric Industries) was heated at 537° C. and RX SP CG TM (Jeneric Industries) was heated at 1093° C.; in Step 4, the organosilicon compound was applied by placing one drop of the A-174 solution on the surface of the metal disk with a plastic transfer pipet; and in Step 5, the samples were heated in the porcelain furnace described in Step 3a at 500° C. for 10 minutes.

The treated samples were prepared for adhesion testing using the general procedure of EXAMPLE 1, except that in Step A, one drop of the A-174 solution of Step 4 was used, in Step B, the SILUX enamel bond was cured for 10 seconds, and in Step C, P-30 TM restorative (3M) was used as the adhesive and was cured for 40 seconds.

In TABLE II are listed the shear adhesion values for each of the metal surfaces prepared as detailed above and the values obtained when the corresponding metals were treated using the commercially available SILICOATER TM (Model #5112113, Kulzer, Friedrichsdorf, Germany) according to the manufacturer's instructions. The shear adhesion values of 10 samples were averaged to give the values in TABLE II.

TABLE II

| | Adhesion to Metal Surfaces | |
|---|---|---|
| | Shear Adhesion (Kg/cm$^2$) | |
| Type of Metal Surface | Example 2 | Silicoater |
| REXILLIUM TM III* | 365 | 240 |
| Stainless Steel 316 | 350 | 290 |
| RX NATURELLE TM ** | 196 | 150 |
| RX SP CG TM *** | 80 | 30 |

*Composition by weight: Be, 1.8%; Cr, 12-15%; Mo, 4-6%; Ni, 74-78%
**Composition by weight: Gold, 2%; Palladium, 13%
***Composition by weight: Gold, 75%; Palladium, 13%

The data in TABLE II show the higher shear adhesion values were obtained on various metal surfaces using the procedure detailed above than were obtained using the SILICOATER method.

EXAMPLE 3

Samples of REXILLIUM III were treated using the procedure of EXAMPLE 2 modified as set out in TABLE III below.

TABLE III

| Surface Preparation | Shear Adhesion (Kg/cm$^2$) |
|---|---|
| Non-sandblasted, Steps 2, 3a, 4 & 5 omitted | 50 |
| Non-sandblasted, Step 2 omitted | 200 |
| Sandblasted, Steps 3a, 4 and 5 omitted | 200 |
| Sandblasted, no steps omitted | 365 |

The data of TABLE III show that the combination of sandblasting, heating of the metal surface, and pyrolysis of a coating of organosilicon compound to afford a layer of silicon oxides yields optimal shear adhesion values.

EXAMPLE 4

Stainless steel orthodontic brackets (No. 064-008, American Orthodontics, Sheboygan, Wis.) with no undercuts or steel mesh, having an approximate bonding base surface area of 0.17 cm$^2$, were subjected to various treatments set forth below.

Treatment A consisted of rinsing the brackets with acetone, allowing to dry, coating with SCOTCHPRIME TM ceramic primer (a silanol priming solution, 3M), drying in air and heating in the porcelain furnace described in EXAMPLE 2 for four hours at 500° C.

Treatment B consisted of rinsing the brackets with acetone, drying, sandblasting with a PONY TM Sandblaster (Buffalo Dental, Syosset, N.Y.) containing silica sand at nominal size 60–80 microns, acid etching for 2 minutes with a 50:50 (by weight) solution of sulfuric acid:deionized water, rinsing with deionized water, blow drying, and heating in the porcelain furnace described in EXAMPLE 2 at 500° C. for 10 minutes.

The Control consisted of rinsing the brackets with acetone, drying in air, acid etching for 2 minutes with a 50:50 (by weight) solution of sulfuric acid:deionized water, rinsing with deionized water, and blow drying.

Each prepared bracket was bonded to a bovine tooth using the following procedure:

i. Cleaning the enamel surface of the bovine tooth for 10–20 seconds with aluminum oxide prophy paste [prepared by mixing approximately equal volumes of water and a fine powdered pumice (Moyco Industries, Inc., Philadelphia, Pa.)], rinsing with deionized water, and blow drying;

ii. Acid etching the tooth with SCOTCHGEL enamel etchant for 60 seconds, rinsing with deionized water, and blow drying;

iii. Coating the treated surface of the bracket with one drop of SCOTCHPRIME ceramic primer and drying in air;

iv. Applying SILUX enamel bond adhesive to the prepared tooth of Step ii and blowing with air to thin the coating layer;

v. Applying TRANSBOND light cure orthodontic adhesive to the base of the bracket of Step iv;

vi. Pressing the adhesive coated bracket onto the prepared bovine tooth and removing excess peripheral adhesive;

vii. Curing with a VISILUX 2 curing light for 30 seconds with the tip of the light guide positioned directly above the bracket;

viii. After about a 5 minute delay, placing the tooth with the bracket adhered thereto in deionized water at 37° C. for about 16 hours; and ix. Removing the tooth with the bracket adhered thereto from the water and measuring the shear adhesion using the procedure of Step D of EXAMPLE 1, except that the tooth was attached to the lower jaw of the tensile testing machine with a fixture capable of holding the root of the tooth vertically rigid during the testing procedure.

TABLE IV shows the shear adhesion values of Treatment A, Treatment B and the Control. Treatment A was run using 10 samples and Treatment B and the Control were run using 5 samples. The values for each treatment were averaged to provide the shear adhesion values in TABLE IV.

TABLE IV

| Shear Adhesion to Brackets (Kg/cm²) | | |
|---|---|---|
| Treatment A | Treatment B | Control |
| 70 | 59 | 8 |

The data in TABLE IV show that Treatment A, involving the pyrolysis of an organosilicon compound, provides a high level of adhesion relative to treatments not involving such pyrolysis.

EXAMPLE 5

Endodontic posts (No. 5, 316L Stainless, 3M Unitek) were treated using the following steps:

5-1. Acid etching for 45 seconds with a 37% solution of phosphoric acid, rinsing with water and drying in air;

5-2. Coating with SCOTCHPRIME ceramic primer and drying in air; and 5-3. Heating in the muffle oven described in step 5 of EXAMPLE 1 for 10 minutes at 250° C. or 500° C. as indicated in TABLE V below.

The above treated samples were prepared for adhesion testing using the following procedure:

5-A. Coating the prepared surface with SCOTCHPRIME ceramic primer and drying in air;

5-B. Brushing onto the bottom 3 mm of the post a Bis-GMA/TEGDMA dual-cure luting cement comprising about 60% by weight of a quartz filler. The cement was incrementally applied to provide a spherical mass of approximately 4 mm diameter.

The posts were stored for 5 days in water at 37° C. The force in kg required to remove the post from the resin was measured using an INSTRON apparatus.

The data in TABLE V show the effect of heating the treated posts independently at 250° C. and 500° C. The "Untreated" group consisted of posts treated according to Steps 5-B and 5-C only. The "Silane on Untreated Post" group consisted of posts treated according to the above procedure, except that Steps 5-1, 5-2 and 5-3 were omitted. The adhesion values for four to six samples were averaged for each group.

TABLE V

| | Removal Force (Kg) |
|---|---|
| Untreated | 6 |
| Silane on untreated post | 9 |
| Silane treatment, 250° C. heating | 15 |
| Silane treatment, 500° C. heating | 21 |

The data show that treating with an organosilicon compound and heating at either 250° C. or 500° C. provided increased adhesion values.

EXAMPLE 6

A design experiment was conducted on samples of type 303 stainless steel, each in the form of a circular disk 2.54 cm in diameter, using three concentrations of A-174 silane solution, three oven temperatures and three heating times. The procedure of EXAMPLE I was used with the following changes: Step 2 was omitted; for Step 4, 5 µL of the hydrolyzed A-174 silane solution was used; for Step 5, various oven temperatures and times were used; and for Step A, two 5 µL coatings of a 1% solution of A-174 silane were used on each specimen. Six specimens were run for each sample number and the shear adhesion values were averaged. TABLE VI sets out the conditions used as well as the respective adhesion values obtained.

TABLE VI

| Sample No. | % A-174 TM | Oven Temp. (°C.) | Heating Time (Min.) | Adhesion (Kg/cm²) |
|---|---|---|---|---|
| 1 | 0.5 | 300 | 5 | 57 |
| 2 | 0.5 | 700 | 5 | 41 |
| 3 | 0.5 | 300 | 20 | 26 |
| 4 | 0.5 | 700 | 20 | 27 |
| 5 | 2.0 | 300 | 5 | 127 |
| 6 | 2.0 | 700 | 5 | 32 |
| 7 | 2.0 | 300 | 20 | 87 |
| 8 | 2.0 | 700 | 20 | 41 |
| 9 | 1.0 | 500 | 10 | 46 |
| 10 | 1.0 | 500 | 10 | 42 |
| 11 | 1.0 | 500 | 10 | 38 |
| 12 | 1.0 | 500 | 10 | 41 |

The data of TABLE VI were statistically analyzed using analysis of variance. Statistical analysis showed that the highest adhesion values were produced using the highest concentration of the A-174 silane solution, the lowest oven temperature and the shortest heating time.

EXAMPLE 7

Various organosilicon compounds were independently applied to the surface of REXILLIUM III using the procedure of EXAMPLE 2. TABLE VII sets out the compounds used and the respective adhesion values obtained.

TABLE VII

| Organosilicon Compound | Shear Adhesion (Kg/cm²) |
|---|---|
| A-174 TM neat* | 365 |
| SCOTCHPRIME TM (hydrolyzed A-174 TM silane) | 365 |
| Hydrolyzed A-1100 TM silane** | 235 |

*3-methacryloxypropyltrimethoxysilane
**3-aminopropyltriethoxysilane

The data in TABLE VII show that different organosilicon compounds can be used to achieve high shear adhesion values to REXILLIUM III.

EXAMPLE 8

Samples of type 303 and type 17-4 stainless steel, each in the form of a circular disk 2.54 cm in diameter, were treated with a silane solution. The procedure of EXAMPLE 1 was followed except that in Step 4 the volume of A-174 silane solution was varied from 5 to 120 µL. TABLE VIII sets out the shear adhesion values for the average of six samples at the various volumes of silane solution applied.

TABLE VIII

| Volume (μL) | Stainless Steel 303 (Kg/cm²) | Stainless Steel 17-4 (Kg/cm²) |
| --- | --- | --- |
| 5 | 237 | 162 |
| 10 | 316 | 263 |
| 15 | 315 | 178 |
| 20 | 327 | 235 |
| 30 | 363 | 304 |
| 60 | 311 | 283 |
| 120 | 265 | 207 |

The data in TABLE VIII show that the maximum shear adhesion values are obtained when solution volumes of 10 to 60 μL are used.

The claimed invention is:

1. A method for applying a layer of exogenous inorganic oxide to the surface of a metal article, which method comprises the steps of:
   (a) coating at least a portion of the surface of the metal article with an organosilicon compound that is capable on heating of forming silica; and
   (b) heating the coated surface at a temperature and for a time sufficient to convert the coating to a layer of silica.

2. A method according to claim 1, further comprising the preliminary step of roughening the surface.

3. A method according to claim 2, wherein the roughening step comprises sandblasting.

4. A method according to claim 1, further comprising the preliminary steps of
   (i) roughening the surface; and
   (ii) heating the roughened surface at a temperature and for a time sufficient to form an oxide layer on said surface.

5. A method for adhering a metal article to an adhesive and/or a composite, which method comprises the steps of:
   (a) coating at least a portion of the surface of the article with an organosilicon compound that is capable on heating of forming silica;
   (b) heating the coated surface at a temperature and for a time sufficient to convert the coating to a layer of silica; and
   (c) adhering the metal article at said layer of silica to the adhesive and/or composite.

6. A method according to claim 5, further comprising between steps (b) and (c) the step of applying a coupling agent to the layer of silica.

7. A method according to claim 5, further comprising the preliminary step of roughening the surface intended to be adhered to the adhesive and/or composite.

8. A method according to claim 5, wherein the roughening step comprises sandblasting.

9. A method according to claim 5, further comprising the preliminary steps of
   (i) roughening the surface intended to be adhered to the adhesive and/or composite; and
   (ii) heating the roughened surface intended to be adhered to the adhesive and/or composite at a temperature and for a time sufficient to form an oxide layer on said surface.

10. A method for adhering a metal article to a substrate by way of an intermediate layer of adhesive, which method comprises the steps of:
    (a) coating at least a portion of the surface of the article with an organosilicon compound that is capable on heating of forming exogenous inorganic oxide;
    (b) heating the coated surface at a temperature and for a time sufficient to convert the coating to a layer of silica;
    (c) adhering the article at said layer of silica to an intermediate layer of adhesive composite; and
    (d) adhering the substrate to the metal article by way of the intermediate layer.

11. A method according to claim 10, further comprising between steps (b) and (c) the step of applying a coupling agent to the layer of silica.

12. A method according to claim 10, further comprising the preliminary step of roughening the surface intended to be adhered to the adhesive.

13. A method according to claim 10, wherein the roughening step comprises sandblasting.

14. A method according to claim 10, further comprising the preliminary steps of
    (i) roughening the surface intended to be adhered to the adhesive; and
    (ii) heating the roughened surface intended to be adhered to the adhesive at a temperature and for a time sufficient to form an oxide layer on said surface.

* * * * *